(12) United States Patent
Selander

(10) Patent No.: US 10,737,050 B2
(45) Date of Patent: Aug. 11, 2020

(54) OXYGEN BOOST DURING MECHANICAL VENTILATION OF A PATIENT

(71) Applicant: MAQUET CRITICAL CARE AB, Solna (SE)

(72) Inventor: Daniel Selander, Sollentuna (SE)

(73) Assignee: MAQUET CRITICAL CARE AB, Solna (SE)

( * ) Notice: Subject to any disclaimer, the term of this patent is extended or adjusted under 35 U.S.C. 154(b) by 405 days.

(21) Appl. No.: 15/736,256

(22) PCT Filed: Jun. 25, 2015

(86) PCT No.: PCT/SE2015/050739
§ 371 (c)(1),
(2) Date: Dec. 13, 2017

(87) PCT Pub. No.: WO2016/209129
PCT Pub. Date: Dec. 29, 2016

(65) Prior Publication Data
US 2018/0154102 A1   Jun. 7, 2018

(51) Int. Cl.
*A61M 16/10*      (2006.01)
*A61M 16/12*      (2006.01)
(Continued)

(52) U.S. Cl.
CPC .... *A61M 16/1015* (2014.02); *A61M 16/0051* (2013.01); *A61M 16/024* (2017.08);
(Continued)

(58) Field of Classification Search
CPC .............. A61M 16/00; A61M 16/0003; A61M 16/0051; A61M 16/0057; A61M 16/006;
(Continued)

(56) References Cited

U.S. PATENT DOCUMENTS 5,071,453 A * 12/1991 Hradek ..................... A62B 7/14
                                                                95/19
5,848,591 A * 12/1998 Weismann ............ A61M 16/12
                                                             128/204.22
(Continued)

FOREIGN PATENT DOCUMENTS

CN    101484202    7/2009
EP    1 205 203    5/2002
(Continued)

*Primary Examiner* — Bradley H Philips
*Assistant Examiner* — Vincent D Hoang
(74) *Attorney, Agent, or Firm* — Fay Kaplun & Marcin, LLP

(57) ABSTRACT

A ventilator delivers breathing gas to a patient via a patient circuit connecting the ventilator and the patient. The ventilator is configured to, upon activation of an oxygen boost function of the ventilator, increase the oxygen concentration of the breathing gas so as to deliver oxygen-enriched breathing gas to the patient. The ventilator includes a control unit configured to determine the volume of a part of the patient circuit conveying breathing gas from the ventilator to the patient, determine a delay in delivery of the oxygen-enriched breathing gas to the patient based on the volume, and cause indication of the delay to an operator of the ventilator.

15 Claims, 4 Drawing Sheets

(51) Int. Cl.
*A61M 16/16* (2006.01)
*A61M 16/08* (2006.01)
*A61M 16/00* (2006.01)

(52) U.S. Cl.
CPC .... *A61M 16/0833* (2014.02); *A61M 16/0883* (2014.02); *A61M 16/12* (2013.01); *A61M 16/16* (2013.01); *A61M 2016/1025* (2013.01); *A61M 2202/0208* (2013.01); *A61M 2205/505* (2013.01); *A61M 2205/584* (2013.01)

(58) Field of Classification Search
CPC .......... A61M 16/0063; A61M 16/0066; A61M 16/0069; A61M 16/0072; A61M 16/0075; A61M 16/0078; A61M 16/0081; A61M 16/0084; A61M 16/021; A61M 16/022; A61M 16/024; A61M 16/1015; A61M 2016/0015; A61M 2016/0018; A61M 2016/0021; A61M 2016/0024; A61M 2016/0027; A61M 2016/0033; A61M 2016/0036; A61M 2016/0039; A61M 2016/0042; A61M 2205/33; A61M 2205/3327; A61M 2205/3331; A61M 2205/3334; A61M 2205/3379; A61M 2230/435

See application file for complete search history.

(56) References Cited

U.S. PATENT DOCUMENTS

| | | | |
|---|---|---|---|
| 6,186,142 B1* | 2/2001 | Schmidt | A61M 16/08 128/204.23 |
| 2011/0088693 A1 | 4/2011 | Somervell et al. | |
| 2012/0006326 A1* | 1/2012 | Ahmad | A61M 16/12 128/204.22 |
| 2013/0104896 A1* | 5/2013 | Kimm | A61M 16/00 128/204.23 |
| 2015/0059764 A1 | 3/2015 | Metelits | |
| 2015/0107588 A1 | 4/2015 | Cheung et al. | |
| 2015/0144130 A1 | 5/2015 | O'Donnell et al. | |

FOREIGN PATENT DOCUMENTS

| | | |
|---|---|---|
| WO | 2003/063939 | 8/2003 |
| WO | 2006/004626 | 1/2006 |
| WO | 2015/038014 | 3/2015 |
| WO | 2010/109364 | 9/2016 |

* cited by examiner

OXYGEN BOOST DURING MECHANICAL VENTILATION OF A PATIENT

TECHNICAL FIELD

The present disclosure relates to a ventilator, method and computer program for temporary provision of increased oxygen concentration to a patient during mechanical ventilation, often referred to as oxygen boost.

It also relates to a ventilator, method and computer program for automatic determination of the presence of any humidifier in the inspiratory line of a patient circuit to which the ventilator is connected.

BACKGROUND

Most modern ventilators offer a function, herein referred to as "oxygen boost", which allows the operator of the ventilator to temporarily increase the oxygen concentration of the breathing gas delivered to the patient. Typically, when the operator activates the oxygen boost function, the ventilator automatically increases the fraction of delivered oxygen by a fixed amount for a fixed period of time, e.g. by having the ventilator delivering 100% oxygen instead of air for one minute of time.

However, it is difficult in clinical practice to foresee the effect of such an oxygen boost since it is difficult to know how the increase in ventilator-delivered fraction of oxygen affects the oxygen concentration in the breathing gas actually reaching the patient, at least unless monitoring said oxygen concentration by means of an oxygen sensor disposed in the proximity of the patient, e.g. in or near the Y-piece of the patient circuit connecting the patient and the ventilator.

Often, there is a considerable delay in oxygen concentration increase in the breathing gas reaching the patient. In fact, during ventilation treatment of neo-patients where tidal volumes are small compared to the volumes of hoses and additional equipment such as humidifiers, there may be a delay in delivery of increased oxygen concentration to the patient of nearly one minute, meaning that there may be no or nearly no increase in oxygen concentration in the breathing gas delivered to the patient even one minute after activation of the oxygen boost function.

Often, clinicians are mislead by the erroneous conception that activation of the oxygen boost function causes a momentary increase in oxygen concentration to a preset level (oxygen boost level), and that breathing gas with an oxygen concentration corresponding to said oxygen boost level is delivered to the patient from the activation of the oxygen boost function and for a set period of time during which the oxygen boost function is activated (oxygen boost duration).

This misconception may give rise to situations in which activation of the oxygen boost function does not have the desired effect on the ventilated patient. In some cases, for example in situations in which the oxygen boost function is activated in order to temporarily increase the patient's blood oxygen levels before disconnecting the patient from the ventilator, the unawareness of this delay may put the patient in a state of hypoxia.

US 2013/0104896 A1 discloses a medical ventilator system including oxygen boost functionality, in which the oxygen saturation level of blood in the patient is monitored during activation of the oxygen boost function. If the monitored oxygen saturation level exceeds a predetermined threshold value, the delivered oxygen concentration can be adjusted.

This functionality serves to prevent the patient from receiving too much oxygen during activation of the oxygen boost function. However, it does not prevent the patient from receiving too little oxygen. Furthermore, it requires monitoring of the oxygen saturation level of the patient's blood to realize the delayed effect of activation of the oxygen boost function.

SUMMARY

It is an object of the present invention to provide a ventilator with improved oxygen boost functionality, solving or at least mitigating one or more of the above mentioned shortcomings of oxygen boost functionality of ventilators according to prior art.

In particular it is an object of the present invention to minimize the risk of insufficient oxygenation of a patient prior to disconnection of the patient from the ventilator.

Yet another object of the present invention is to provide a ventilator including functionality allowing an operator of the ventilator to better realize the effect of the oxygen boost on the ventilated patient.

These and other objects are achieved by means of a ventilator according to claim 1. They are also achieved according to a method according to claim 13, and a computer program according to claim 14.

According to one aspect of the present disclosure, there is provided a ventilator for delivering breathing gas to a patient via a patient circuit connecting the patient to the ventilator. The ventilator is configured to, upon activation of an oxygen boost function of the ventilator, increase the oxygen concentration of the breathing gas so as to deliver oxygen-enriched breathing gas to the patient via said patient circuit.

The ventilator comprises a control unit that is configured to determine the volume of a part of said patient circuit conveying breathing gas from the ventilator to the patient, hereinafter referred to as the inspiratory line of the patient circuit, and to determine a delay in delivery of said oxygen-enriched breathing gas to the patient based on said volume. The control unit is further configured to cause indication of said delay to an operator of the ventilator.

By indicating to the operator the delay in delivery of oxygen-enriched gas to the patient, the misconception that the patient receives oxygen-enriched gas momentarily upon activation of the oxygen boost function can be avoided. Thereby, the risk of too early disconnection of the patient from the ventilator is reduced.

Preferably, the control unit is configured to calculate, based on said delay, a start point in time at which the oxygen-enriched breathing gas reaches the patient, and to cause indication of said start point in time to the operator of the ventilator.

By indicating to the operator the start point in time of delivery of oxygen-enriched gas to the patient, the operator will better realize the effect of activation of the oxygen boost function on the patient, making the oxygen boost functionality both safer and more user-friendly.

The ventilator is preferably configured to, upon activation of the oxygen boost function, deliver the oxygen-enriched breathing gas during a set period of time, herein referred to as the oxygen boost duration. Said set period of time may be predefined or selectable by the operator of the ventilator. The control unit of the ventilator may be configured to calculate, based on said delay in delivery of oxygen-enriched breathing gas to the patient and said set period of time, a finish point in time at which oxygen-enriched breathing gas has been delivered to the patient for said set period of time, and to cause indication of said finish point in time to the operator of the ventilator. Thus, the control unit may be configured to indicate when all oxygen-enriched breathing gas has been delivered to the patient.

This feature further minimizes the risk of too early disconnection of the patient from the ventilator. By indicating to the operator the point in time at which the entire oxygen boost has been delivered to the patient, the operator becomes aware of the point in time at which the patient is likely to be sufficiently oxygenated.

The control unit may further be configured to cause indication of the time remaining until said finish point in time. Such an indication may be helpful to the operator of the ventilator and further improves the user-friendliness of the oxygen boost function.

In one exemplary embodiment, the control unit of the ventilator may be configured to cause indication of a wash-in-wash-out process of oxygen content in the breathing gas reaching the patient, caused by the activation of the oxygen boost function.

This feature allows the operator of the ventilator to continuously follow the course of oxygenation of the patient and thus to better realize the current status of the patient during and after activation of the oxygen boost function.

Preferably, the control unit is configured to cause the indication of the delay in delivery of oxygen-enriched breathing gas to the patient by causing display of an indicator on a display unit of the ventilator or a monitoring system to which the ventilator is connected. This means that the start point in time, the finish point in time, the time remaining until the finish point in time, and/or the wash-in-wash-out process may be visually indicated on said display unit The indicator is preferably a dynamic indicator indicating whether the breathing gas currently reaching the patient is the oxygen-enriched breathing gas or not.

This allows the operator to easily ascertain, at any given time after activation of the oxygen boost function, whether the oxygen-enriched breathing gas has not yet reached the patient, is currently delivered to the patient, or has already been delivered to the patient.

In one exemplary embodiment, the control unit is configured to cause display of an indicator indicating one of at least two colours; one of which represents a state in which oxygen-enriched breathing gas is delivered to the patient and one of which represents a state in which non-oxygen-enriched breathing gas is delivered to the patient. The control unit causes the indicator to indicate, upon activation of the oxygen boost function, one of said at least two colours in dependence of whether the breathing gas currently reaching the patient is oxygen-enriched or not.

Typically but not necessarily, the ventilator is configured to, upon activation of the oxygen boost function, increase the oxygen concentration of the breathing gas to a set level of oxygen concentration to be delivered to the patient, herein sometimes referred to as the oxygen boost level. The oxygen boost level may be predefined (e.g. to 100% oxygen) or selectable by the operator of the ventilator. In this instance, it should be appreciated that "oxygen-enriched breathing gas" may refer to breathing gas having said set level of oxygen concentration.

Thus, the ventilator of the present disclosure is typically configured to, upon activation of the oxygen boost function, increase the oxygen concentration of the breathing gas to a set level of oxygen concentration (oxygen boost level) to be delivered to the patient during a set period of time (oxygen boost duration). For example, the oxygen boost function may be predefined or set by a an operator of the ventilator to an oxygen boost level of 100% oxygen and an oxygen boost duration of 1 minute.

Although typically being delivered during a set period of time, embodiments in which the ventilator, upon activation of the oxygen boost function, delivers oxygen-enriched breathing gas until manual deactivation of the oxygen boost function by the operator of the ventilator are also contemplated by the present disclosure. In this case too, indication of the delay in delivery of oxygen-enriched breathing gas to the patient may be helpful and support the operator in the decision on when to manually deactivate the oxygen boost function in order to avoid insufficient oxygenation of the patient.

Besides the volume of the inspiratory line of the patient circuit, the control unit typically uses the volume per time unit of breathing gas delivered by the ventilator in the determination of the delay of delivery of oxygen-enriched breathing gas to the patient, i.e. the current minute ventilation of the patient provided by the ventilator. This quantity may be a set parameter that is set by an operator of the ventilator, or calculated by the control unit based on other known parameters, such as tidal volume and respiratory rate settings of the ventilator.

Preferably, the control unit is also configured to take leakage into account in the calculation of the delay in delivery of oxygen-enriched breathing gas to the patient. Leakage typically occurs in the interface between the patient and the patient circuit, i.e. between the patient and the patient connector. The control unit may hence be configured to determine the leakage of the patient circuit, including patient connector leakage, and to determine the delay in delivery of oxygen-enriched breathing gas to the patient based on the volume of the inspiratory line, the current minute ventilation of the patient, and any leakage in the inspiratory line, including patient connector leakage. Basically, this means that the control unit may be configured to calculate the delay based on the volume of the inspiratory line of the patient circuit and the net ventilation of the patient.

In some embodiments, the control unit may be configured to determine the volume of the inspiratory line of the patient circuit based on user input received by the ventilator from an operator thereof, which user input is indicative of the volume of the inspiratory line of the patient circuit.

Preferably, however, the control unit is configured to automatically determine the volume of the inspiratory line of the patient circuit. The volume of the inspiratory line may be automatically determined by the control unit based on a pressure/volume relationship of the patient circuit.

For example, the control unit may be configured to determine the volume of the inspiratory line based on measured pressure changes in the patient circuit in response to changes in gas volume in the patient circuit, i.e. based on a gas pressure response to a change in gas volume in the patient circuit, hereinafter referred to as a pressure-to-volume response of the patient circuit.

The control unit may be configured to use said pressure-to-volume response in order to calculate the compliance of the gas occupying the patient circuit prior to introduction of gas into the inspiratory line thereof, and to determine the volume of the inspiratory line of the patient circuit based on said calculated compliance, e.g. by using known information on ambient pressure (the pressure surrounding the patient circuit).

Preferably, the control unit is configured to determine the volume of the inspiratory line of the patient circuit during a pre-use check of the ventilator. For example, during such a pre-use check, the control unit may be configured to cause changes in the gas volume in the patient circuit, e.g. by controlling an inspiratory valve of the ventilator to permit a flow of pressurized gas into the inspiratory line of the patient circuit while preventing gas from flowing out of the proximal and expiratory part of the patient circuit, determine said pressure-to-volume response based on pressure measurements indicative of the gas pressure in the patient circuit, and estimate the volume of the inspiratory line of the patient circuit based on said pressure-to-volume response. Prevention of gas from flowing out of the proximal and expiratory part of the patient circuit may for example be achieved through manual occlusion of the proximal part of the patient circuit, e.g. a Y-piece or a patient connector, and closure of an expiratory valve of the ventilator.

The control unit is typically configured to first determine the total volume of the patient circuit based on said pressure-to-volume response, i.e. the volume of both the inspiratory line of the patient circuit conveying breathing gases from the ventilator to the patient and an expiratory line of the patient circuit conveying expiration gases from the patient to the ventilator, and to determine the volume of the inspiratory line based on the total volume of the patient circuit. For example, the control unit may be configured to estimate the volume of the inspiratory line as 50% of the total volume of the patient circuit in cases where no humidifier is connected in the inspiratory line and as more than 50% of said total volume in cases where a humidifier is connected in the inspiratory line.

Humidifiers for active humidification of breathing gas are often connected in line with the inspiratory line of the patient circuit, in particular during ventilatory treatments of neonates and infants. The use of such humidifiers typically adds considerable volume to the inspiratory line, which further increases the delay of the effect of activation of the oxygen boost function.

The control unit of the present disclosure may be configured to determine if the inspiratory line comprises a humidifier, and to determine the volume of the inspiratory line based also on the presence of any humidifier.

The control unit may be configured to determine if the inspiratory line comprises a humidifier based on user input received by the ventilator from an operator thereof, which user input is indicative of the presence of a humidifier.

Preferably, however, the control unit is configured to automatically determine if the patient circuit comprises a humidifier. This functionality is advantageous when it comes to improving the oxygen boost functionality of the ventilator as it improves the accuracy in the determination of the volume of the inspiratory line of the patient circuit. However, automatic detection of the presence of a humidifier in a patient circuit of a ventilation system may be advantageous also for other purposes and it should thus be realised that this aspect of the present disclosure forms a separate invention which may be independent from the oxygen boost functionality subject to the present application.

Thus, according to an independent aspect of the present disclosure, there is provided a ventilator capable of automatically determining if a patient circuit for connecting the ventilator with a patient to be ventilated comprises a humidifier. To this end, the ventilator comprises a control unit configured to cause a change in composition of gas in the patient circuit through the supply into an inspiratory line of the patient circuit of a gas having a different composition than another gas previously occupying the patient circuit. The control unit is further configured to determine a rate of change in gas composition downstream a part of said inspiratory line, e.g. from gas composition measurements obtained downstream said part of the inspiratory line, and to determine if a humidifier is present in said part of the inspiratory line based on said rate of change in gas composition. The gas first occupying the patient circuit will hereinafter be referred to as the first gas, while the gas that is introduced by the ventilator into the inspiratory line to cause the change in composition of gas in the patient circuit will be referred to as the second gas.

If a humidifier is present in said part of the patient circuit, the relatively large volume of the humidifier will serve as a mixing chamber, increasing the mixture of the first gas originally occupying the patient circuit and the second gas supplied by the ventilator. Therefore, the change in gas composition per time unit caused by the introduction of gas into the inspiratory line of the patient circuit, measured downstream the location of the humidifier (if any), is indicative of the presence of any humidifier. A quick rate of change, i.e. a big change in measured gas composition per time unit, indicates a relatively low degree of gas mixing in the part of the patient circuit that is located upstream the point of measurement, and so the absence of any humidifier in said part of the patient circuit. A slow rate of change, i.e. a small change in measured gas composition per time unit, indicates a relatively high degree of gas mixing in the part of the patient circuit that is located upstream the point of measurement, and so the presence of a humidifier in said part of the patient circuit.

The rate of change in measured gas composition will hereinafter be referred to as the "response to the change in gas composition", caused by the introduction of the second gas into the inspiratory line of the patient circuit. A quick response corresponds to a high rate of change in gas composition at the location of the gas composition measurement and so indicates the absence of a humidifier, while a slow response corresponds to a low rate of change in gas composition at the location of the gas composition measurement and so indicates the presence of a humidifier.

The control unit may hence be configured to determine the response to the change in gas composition based on gas composition measurements obtained downstream a part of the inspiratory line of the patient circuit, and to determine if a humidifier is present in said part of the inspiratory line based on said response.

Preferably, the control unit is configured to determine a step response to the change in gas composition, which step response is indicative of a mean rate of change in measured gas composition from a first gas composition to a second gas composition (not necessarily corresponding to the compositions of the first and second gases), and to determine if a humidifier is present in said part of the patient circuit based on said step response. The step response may for example be the time required to change the composition of the gas measured upon from the first gas composition to the second gas composition.

For example, the gas meter may be an oxygen sensor and the control unit may be configured to cause a change in composition of gas in the patient circuit from air (21% oxygen) to oxygen (100%) through the introduction of 100% oxygen into the inspiratory line of an air-containing patient circuit. An exemplary step response on which determination may be based is the time required to cause a change in oxygen concentration from a first oxygen concentration (e.g. the initial oxygen concentration of 21%) to a second oxygen concentration (e.g. 90%)

In one embodiment, the determination of the presence of any humidifier in the patient circuit is carried out during the above mentioned pre-use check of the ventilator, during occlusion of a proximal part of the patient circuit, e.g. the Y-piece or a patient connector connected to the Y-piece. The determination may be based on gas composition measurements obtained by a gas meter communicatively connected to the control unit and arranged downstream the part of the patient circuit in which a humidifier may be located, e.g. in the Y-piece of the patient circuit, an expiratory line of the patient circuit or an expiratory module of the ventilator.

Preferably, the control unit is further configured to automatically determine the (total) volume of the patient circuit in accordance with the above discussed principles, and to use also the thus determined patient circuit volume in the determination of the presence of any humidifier in the inspiratory line. If the response to the change in gas composition is slow and the determined patient circuit volume is bigger than a "normal" patient circuit volume, then the inspiratory line of the patient circuit is even more likely to comprise a humidifier. Likewise, if the response to the change in gas composition is quick and the determined patient circuit volume substantially equals the volume of a "normal" patient circuit volume, then the inspiratory line of the patient circuit is even more unlikely to comprise a humidifier. Thus, taking the determined volume of the patient circuit into account provides for a more robust determination of the presence of any humidifier in the patient circuit.

In order to determine what is to be considered a "normal" patient circuit volume, the control unit may further be configured to determine the type of patient circuit currently connected to the ventilator, and to determine whether the determined patient circuit volume is bigger than normal or not based on the determined type of the patient circuit. For example, the ventilator may comprise a digital memory storing a plurality (i.e. two or more) of reference values of typical volumes of different types of breathing circuits. In order to determine whether the determined patient circuit volume is bigger than normal or not, the control unit may be configured to compare the determined patient circuit volume with the reference value associated with the determined type of patient circuit. Typically, the patient circuit is either an adult type of patient circuit or a neonatal (pediatric) type of patient circuit. Thus, in one embodiment, the control unit may be configured to determine whether the patient circuit currently connected to the ventilator is an adult patient circuit or a neonatal patient circuit, and to determine whether the determined volume of the patient circuit is bigger than normal or not based on a comparison with one of at least two reference values indicative of the volume of a typical adult patient circuit and the volume of a typical neonatal patient circuit, selected in dependence of the determined type of the patient circuit.

In order to determine the type of the patient circuit currently connected to the ventilator, the ventilator may comprise a radio receiver, such as an RFID reader, configured to receive information related to the type of the patient circuit from a radio transmitter of the patient circuit, such as an RFID tag, when said patient circuit is connected to the ventilator.

Preferably, however, the control unit is configured to determine the resistance of the patient circuit, and to determine the type of the patient circuit based on said resistance. High resistance is indicative of a neonatal patient circuit and low resistance is indicative of an adult patient circuit. The resistance of the patient circuit may be automatically determined by the control unit based on pressure and flow measurements obtained in the patient circuit and/or the ventilator, as well known in the art.

Thus, in one embodiment, the control unit is configured to determine the presence of any humidifier in the inspiratory line of the patient circuit based on the response to the change in gas composition, the volume of the patient circuit, and the type of the patient circuit. When the type of patient circuit is determined from the patient circuit resistance, this means that the presence of any humidifier in the inspiratory line of the patient circuit is determined by the control unit based on the response to the change in gas composition, the volume of the patient circuit, and the resistance of the patient circuit.

Referring again to the improved oxygen boost function discussed above, once the control unit has established whether or not the inspiratory line of the patient circuit comprises a humidifier, the volume of the inspiratory line can be determined based on the total volume of the patient circuit and the presence of any humidifier, whereby the delay in delivery of the oxygen-enriched breathing gas to the patient can be calculated more precisely.

As mentioned above, the control unit may be configured to estimate the volume of the inspiratory line as more than 50% and preferably 55%-65% of the total volume of the patient circuit in case of presence of a humidifier.

In one exemplary embodiment, when a humidifier is deemed to be present, the control unit may be configured to determine the volume of the inspiratory line as 55%-65% of the total volume of the patient circuit in dependence of the type of the patient circuit currently connected to the ventilator.

In another exemplary embodiment, the control unit may be configured to determine the volume of the inspiratory line based on the total volume of the patient circuit and the volume of the humidifier itself, and more precisely the active volume of the humidifier conveying breathing gas from the ventilator towards the patient (i.e. the volume of the humidifier not filled by water during use thereof). This volume differs between different types of humidifiers but may be assumed by the control unit based on the type of the patient circuit currently connected to the ventilator.

According to yet another aspect of the present disclosure, there is provided a method for providing improved oxygen boost functionality of a ventilator delivering breathing gas to a patient via a patient circuit connecting the ventilator and the patient, which ventilator is configured to, upon activation of an oxygen boost function of the ventilator, increase the oxygen concentration of the breathing gas so as to generate oxygen-enriched breathing gas to be delivered to said patient. The method comprises the steps of determining the volume of a part of said patient circuit conveying breathing gas from the ventilator to the patient; determining a delay in delivery of said oxygen-enriched breathing gas to the patient based on said volume, and causing indication of said delay to an operator of the ventilator.

The method is typically performed by the control unit of the ventilator and may further comprise any of the above mentioned steps performed by said control unit.

The method is typically a computer-implemented method performed by the control unit through execution of a computer program. The computer program may be stored in a non-volatile memory of the ventilator and executed by means of a processing unit, such as a microprocessor, of the ventilator.

Thus, according to another aspect of the present disclosure, there is provided a computer program for providing improved oxygen boost functionality of a ventilator delivering breathing gas to a patient via a patient circuit connecting the ventilator and the patient, which ventilator is configured to, upon activation of an oxygen boost function of the ventilator, increase the oxygen concentration of the breathing gas so as to generate oxygen-enriched breathing gas to be delivered to said patient. The computer program comprises computer-readable program code which, when executed by a processing unit of the ventilator, causes the control unit of the ventilator to perform the above mentioned method steps, i.e. at least to determine the volume of a part of said patient circuit conveying breathing gas from the ventilator to the patient; determine a delay in delivery of said oxygen-enriched breathing gas to the patient based on said volume, and cause indication of said delay to an operator of the ventilator.

According to yet another aspect of the present disclosure, there is provided a method for determining if a patient circuit for connecting a ventilator with a patient to be ventilated comprises a humidifier. The method comprises the steps of causing a change in composition of gas in the patient circuit through the supply into an inspiratory line of the patient circuit of a gas having a different composition than another gas previously occupying the patient circuit, determining a rate of change in gas composition downstream a part of said inspiratory line, and determining if a humidifier is present in said part of the inspiratory line based on said rate of change in gas composition.

This method too is typically performed by the control unit of the ventilator and may further comprise any of the above mentioned steps performed by said control unit.

The method is typically a computer-implemented method performed by the control unit through execution of a computer program. The computer program may be stored in a non-volatile memory of the ventilator and executed by means of a processing unit, such as a microprocessor, of the ventilator.

Thus, according to another aspect of the present disclosure, there is provided a computer program for determining if a patient circuit for connecting a ventilator with a patient to be ventilated comprises a humidifier. The computer program comprises computer-readable program code which, when executed by a processing unit of the ventilator, causes the control unit of the ventilator to perform the above mentioned method steps, i.e. at least to cause a change in composition of gas in the patient circuit through the supply into an inspiratory line of the patient circuit of a gas having a different composition than another gas previously occupying the patient circuit; determine a rate of change in gas composition downstream a part of said inspiratory line, and determine if a humidifier is present in said part of the inspiratory line based on said rate of change in gas composition.

Another advantage of the above described ventilator, capable of automatically determining the total volume of the patient circuit and/or the volume of the inspiratory line of the patient circuit, is that this information may be used as control parameter to ensure correct ventilator settings and/or to serve as decision support for the operator of the ventilator. For example, if the determined total volume of the patient circuit is large (or small) compared to a body weight index (BWI) or tidal volume setting set by the ventilator operator, the ventilator may be configured to generate an alarm and/or to cause display of information informing the operator of the mismatch between the patient circuit volume and the set BWI and/or tidal volume, e.g. by displaying on a display unit of the ventilator a message stating that the patient circuit volume is large (or small) in relation to patient BWI.

More advantageous aspects and effects of the method as well as the gas delivery system and the additive gas delivery apparatus of the invention will be described in the detailed description following hereinafter.

BRIEF DESCRIPTION OF THE DRAWINGS

The present invention will become more fully understood from the detailed description provided hereinafter and the accompanying drawings which are given by way of illustration only. In the different drawings, same reference numerals correspond to the same element.

DETAILED DESCRIPTION

Figure 1A:
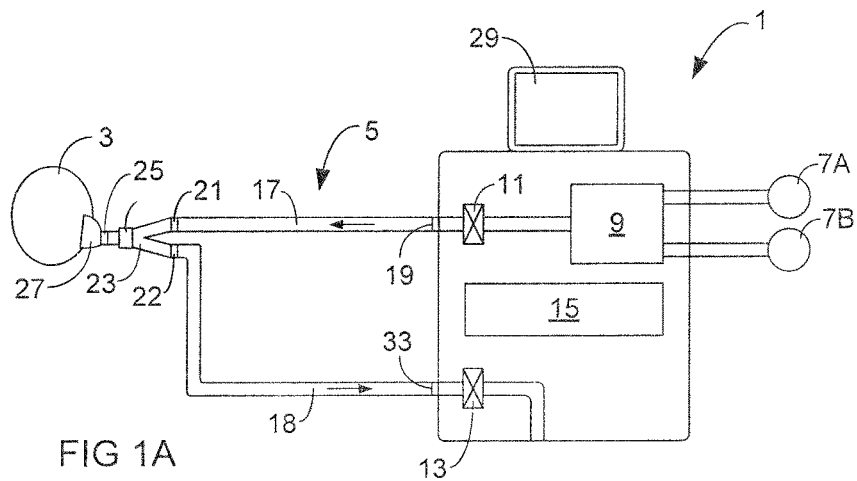
FIG. 1A illustrates a ventilator according to an exemplary embodiment of the present disclosure, connected to a patient circuit through which the ventilator is connected to a patient.

FIG. 1A illustrates a ventilator 1 according to an exemplary embodiment of the present disclosure. In FIG. 1A, the ventilator 1 is connected to a patient 3 via a patient circuit 5 and configured to deliver breaths of pressurized breathing gas to the patient 3. The patient circuit 5 typically comprises a conventional ventilator breathing system (VBS).

The ventilator 1 is configured for delivery of oxygen and at least one further gas or gas mixture to the patient 3. In this exemplary embodiment, the ventilator 1 is connected to two gas sources 7A and 7B, such as wall outlets for the supply of pressurized gas often available in medical care facilities (medical pipeline system), compressors or gas tanks. A first gas source 7A is a gas source for the supply of oxygen and a second gas source 7B is a gas source for the supply of air.

The ventilator 1 comprises a gas mixing module 9 for regulating the composition of the breathing gas to be delivered to the patient 3. The breathing gas composition may be any of at least air (approximately 21% oxygen), oxygen-enriched air (>21% oxygen) and pure oxygen (100% oxygen).

The ventilator 1 further comprises an inspiratory valve 11 for regulating the pressure and/or flow of breathing gas delivered to the patient 3, and an expiratory valve 13 for regulating an expiratory pressure applied to the patient 3 during expiration.

Yet further, the ventilator 1 comprises a control unit 15 for controlling the gas mixing module 9, the inspiratory valve 11 and the expiratory valve 13 based on ventilator settings and sensor data obtained by various sensors of the ventilator.

The patient circuit 5 comprises an inspiratory line for conveying breathing gas from the ventilator 1 to the airways of the patient 3. The inspiratory line comprises an inspiratory length of tubing 17 connecting an inspiratory port (outlet) 19 of the ventilator with an inspiratory port (inlet) 21 of a Y-piece 23, and a part of said Y-piece 23 connecting said inspiratory port 21 with a patient-connection port 25 of the Y-piece, which patient-connection port 25 is connected to a patient connector 27 connecting the patient circuit 5 to the airways of the patient 3. In this exemplary embodiment, the patient connector 27 is a breathing mask. In other embodiments, the patient connector may be a tracheal tube, nasal prongs or any other type of patient connector known in the art. The patient circuit 5 further comprises an expiratory line for conveying expiration gas exhaled by the patient 3 to the ventilator 1. The expiratory line comprises an expiratory length of tubing 18 connecting an expiratory port (outlet) 22 of said Y-piece 23 with an expiratory port (inlet) 33 of the ventilator, and a part of the Y-piece 23 connecting said expiratory port 22 of the Y-piece with the patient-connection port 25 of the Y-piece The ventilator 1 is provided with oxygen boost functionality, meaning that it is configured to temporarily increase the oxygen concentration of the breathing gas delivered to the patient 3 upon activation of an oxygen boost function. In this exemplary embodiment, the ventilator is configured to, upon activation of the oxygen boost function, temporarily increase the oxygen concentration from a baseline level used prior to activation of the oxygen boost function to a desired and increased level of oxygen concentration (herein referred to as the oxygen boost level) and, when a certain time period has elapsed since activation of the oxygen boost function (herein referred to as the oxygen boost duration), return to the baseline level of oxygen concentration. The oxygen boost level is a set level of oxygen concentration which may be predefined (e.g. to 100% oxygen) or selectable by an operator of the ventilator 1.

In some embodiments, the ventilator 1 may be configured to automatically activate the oxygen boost function upon detection of a situation in which certain criteria indicating an increased demand for oxygen by the patient 3 is met, e.g. when at least one sensor-monitored parameter indicative of increased demand for oxygen by the patient 3 exceeds a predetermined threshold value.

Typically, however, the oxygen boost function is activated manually by an operator of the ventilator 1, e.g. by pressing a button causing the oxygen boost function of the ventilator 1 to be activated, such as a touch-button displayed on a touch-sensitive screen of a display unit 29 of the ventilator.

In accordance with the principles of the present disclosure, the ventilator 1 is configured to determine a delay in delivery of the oxygen-enriched gas from the ventilator 1 to the patient 3, based on the volume of the inspiratory line of the patient circuit 5, and to communicate said delay to the operator of the ventilator. The delay is a time period between activation of the oxygen boost function, i.e. the point in time at which the ventilator 1 starts to deliver oxygen-enriched gas (breathing gas having increased oxygen concentration compared to the baseline level of oxygen concentration) to the point in time at which oxygen-enriched breathing gas reaches the patient. In this embodiment in which the ventilator 1 starts to deliver breathing gas having an oxygen concentration corresponding to the oxygen boost level immediately upon activation of the oxygen boost function, the delay may be defined as the time period between activation of the oxygen boost function and reception of the oxygen boost level by the patient 3.

During start-up of the ventilator 1, prior to connection of the patient 3 to the ventilator, the ventilator 5 is configured to perform a pre-use check which may include tests and measurements of internal technical functionality, internal leakage, pressure sensors, flow sensors, gas meters (e.g. oxygen sensors), etc.

The ventilator 1 is configured to determine the volume of the inspiratory line of the patient circuit 5 during said pre-use check, and to use the thus determined inspiratory line volume in the determination of the above mentioned delay, so as to be able to communicate it to the operator of the ventilator, e.g. by communicating the point in time at which the patient 3 starts to receive the oxygen-enriched breathing gas, and/or the point in time at which the patient 3 has received oxygen-enriched breathing gas for a period of time corresponding to the oxygen boost duration.

The control unit 15 of the ventilator 1 is configured to automatically determine the volume of the inspiratory line of the patient circuit 5 through execution of a computer program, stored in a digital memory (not shown) of the ventilator, and executed by a processor (not shown) of the ventilator. The memory and the processor may be comprised in the control unit 15. The computer program may be a software module forming part of a pre-use check software which is automatically executed upon start-up of the ventilator for conducting said pre-use check of the ventilator 1.

The volume of the inspiratory line is typically determined by the control unit 15 based on information related to pressure changes in the patient circuit 5 in response to changes in gas volume in the patient circuit, i.e. a pressure-to-volume response of the patient circuit 5.

Figure 1B:
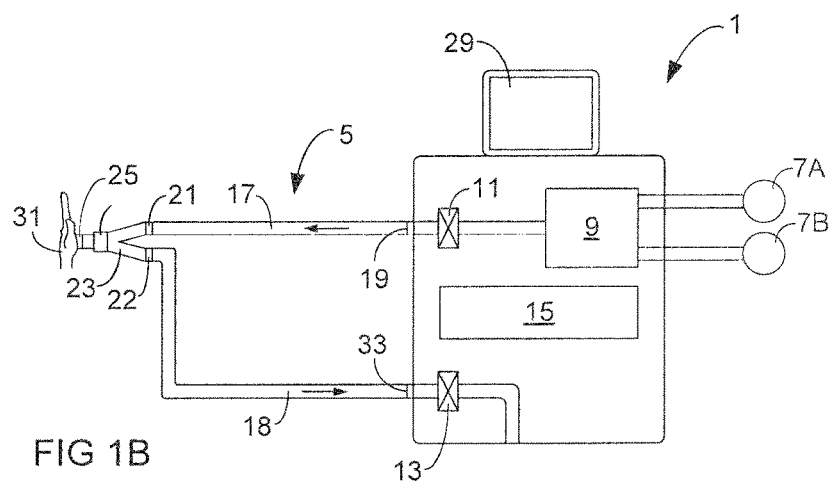
FIG. 1B illustrates the ventilator in FIG. 1A prior to connection to the patient.

FIG. 1B illustrates the ventilator 1 and the patient circuit 5 during execution of the pre-use check of the ventilator 1, prior to connection the patient, at the time of determination of the volume of the inspiratory line of the patient circuit 5.

First, the control unit 15 causes an occlusion instruction to be displayed on the display unit 29, instructing the operator of the ventilator 1 to occlude the proximal part of the patient circuit 5, e.g. by manually occluding the Y-piece or the proximal end of any patient connector already connected to the patient-connection port 25 of the Y-piece 23. This may be achieved by the operator by simply pressing a hand 31 against the proximal part of the patient circuit 5 to make a sealing engagement against the opening thereof. Also, the control unit 15 closes the expiratory valve 13 of the ventilator 1 to prevent any gas introduced into the patient circuit via the inspiratory valve 11 from leaving the patient circuit 5 via the expiratory part thereof.

Then the control unit 15 opens the inspiratory valve 11 to deliver a flow of gas into the patient circuit 5. Typically, the gas used during determination of the volume of the inspiratory line is air. The control unit 15 determines the volume of gas that is introduced into the patient circuit 5, typically from flow measurements obtained by a flow sensor (not shown) located in an inspiratory module of the ventilator 1, between the inspiratory valve 11 and the inspiratory port 19. The control unit 15 is further configured to receive pressure measurements related to the pressure in the patient circuit 5 from at least one pressure sensor (not shown), e.g. a pressure sensor disposed in the Y-piece 23 of the patient circuit 5 or in an expiratory module of the ventilator 1, between the expiratory port 33 of the ventilator and the expiratory valve 13.

The control unit 15 then derives the volume of the patient circuit 5 based on the pressure-to-volume response of the patient circuit, i.e. based on the volume of delivered gas required to cause a certain change in pressure in the patient circuit 5. More precisely, the control unit 15 calculates a compliance value, $C_{tot}$, as:

$$C_{tot} = \Delta V / \Delta P, \quad \text{eq. (1)}$$

where $\Delta V$ is the change in gas volume in the patient circuit 5 (i.e. the volume of gas delivered through the inspiratory valve 11), and $\Delta P$ is the pressure change in the patient circuit caused by said change in gas volume. The thus derived compliance value, $C_{tot}$, is the sum of the compliance of the tubing of the patient circuit 5 ($C_{pc}$) and the compliance of the gas (air) that was present in the patient circuit 5 prior to said change in gas volume ($C_{gas}$), meaning that:

$$C_{tot} = C_{pc} + C_{gas} \quad \text{eq. (2)}$$

The compliance of the gas that was present in the patient circuit 5 prior to said change in gas volume equals the volume of said gas divided by the ambient pressure, i.e.:

$$C_{gas} = V_{gas} / P_{amb}, \quad \text{eq. (3)}$$

where $V_{gas}$ is the volume of the gas (air) that was present in the patient circuit 5 prior to the opening of the inspiratory valve 11, and $P_{amb}$ is the ambient pressure, i.e. the pressure surrounding said gas. The volume of the gas (air) that was present in the patient circuit 5 prior to the opening of the inspiratory valve 11 equals the volume of the patient circuit, i.e.:

$$V_{gas} = V_{pc}, \quad \text{eq. (4)}$$

where $V_{pc}$ is the unknown volume of the patient circuit. Combining equations 1-4 yields:

$$V_{pc} = ((\Delta V / \Delta P) - C_{pc}) * P_{amb} \quad \text{eq. (5)}$$

Thus, assuming that the compliance of the patient circuit tubing ($C_{pc}$) is zero or nearly zero, i.e. that the patient circuit material is stiff, the unknown volume of the patient circuit, $V_{pc}$, can be derived as the quotient $\Delta V/\Delta P$ multiplied by ambient pressure. The ambient pressure may be measured by a sensor that is communicatively connected to the control unit 15, or be assumed by the control unit 15 to be 1 atm (101,325 kPa).

Based on the volume of the patient circuit 5, the control unit 15 may determine the volume of the inspiratory line conveying breathing gas from the ventilator 1 to the patient 3. For example, the control unit may be configured to assume that the volume of the inspiratory line constitutes 50% of the total volume of the patient circuit, meaning that the control unit is configured to determine the volume of the inspiratory line as:

$$V_{insp} = 0.5 * V_{pc}, \quad \text{eq. (6)}$$

where $V_{insp}$ is the volume of the inspiratory line. This is normally a good approximation as the volume of the inspiratory line typically constitutes half or approximately half the total volume of the patient circuit.

However, if a humidifier for humidifying the breathing gas that is to be delivered to the patient is mounted in the inspiratory line, the volume of the inspiratory line (including the volume of the humidifier) typically constitutes substantially more than half the total volume of the patient circuit.

Figure 1C:
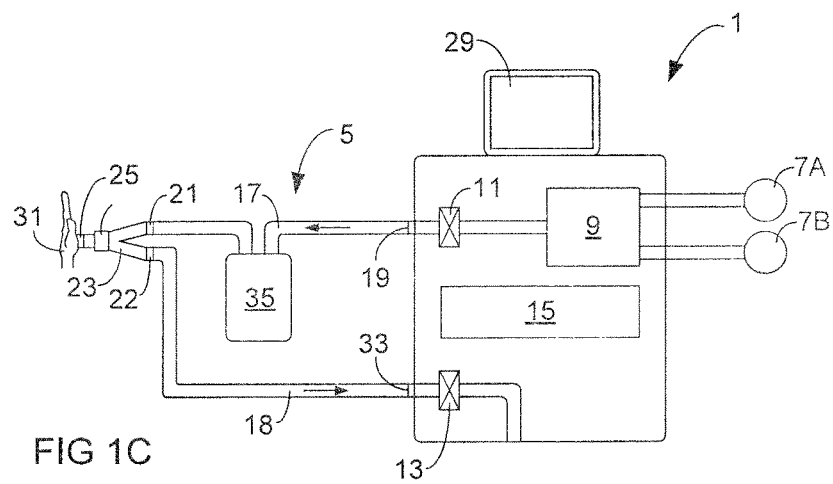
FIG. 1C illustrates the ventilator in FIGS. 1A and 1B connected to another patient circuit comprising a humidifier in an inspiratory line thereof, prior to connection to the patient.

FIG. 1C illustrates a ventilator set up wherein the inspiratory line of the patient circuit 5 comprises a humidifier 35.

In cases where the inspiratory line comprises a humidifier, the control unit 15 of the ventilator may be configured to determine the volume of the inspiratory line (including the humidifier) taking both the calculated total volume of the patient circuit, $V_{pc}$, and the presence of the humidifier into account. This means that the control unit 15, in case of the presence of a humidifier in the inspiratory line of the patient circuit 5, may be programmed to assume that the volume of the inspiratory line of the patient circuit constitutes a major part of the total volume of the patient circuit, i.e. that the volume of the inspiratory line constitutes more than 50% of the total volume of the patient circuit. In one embodiment, the control unit 15 is configured to determine the volume of the inspiratory line as 55%-65% of the calculated total volume of the patient circuit if a humidifier is present.

The control unit 15 may be configured to receive information indicative of the presence of any humidifier from the operator of the ventilator 1, and use this information in the determination of the volume of the inspiratory line.

However, the control unit 15 may also be configured to automatically determine if a humidifier is present in the inspiratory line. Preferably, the automatic determination of the presence of any humidifier in the patient circuit is also conducted by the control unit 15 during the pre-use check of the ventilator 1, and during occlusion of the proximal part of the patient circuit 5.

Automatic determination of whether a humidifier is present in the inspiratory line of the patient circuit 5 may be made based on a measured rate of change in gas composition, caused by introduction through the inspiratory line of the patient circuit of a gas having a different composition than another gas currently occupying the patient circuit, measured downstream a part of the patient circuit in which a humidifier may be present.

To this end, the control unit 15 is configured to cause a change in composition of the gas within the patient circuit 5 through introduction into the inspiratory line of the patient circuit 5 of a gas being different than a gas currently present in the patient circuit, and to determine if a humidifier is present in in a part of the inspiratory line by determining the rate of change in gas composition downstream said part of the inspiratory line, e.g. from gas composition measurements obtained by a gas sensor located in the Y-piece 23 or in an expiratory module of the ventilator 1.

In one embodiment, the above described volume determination is made using air, meaning that the pressure-to-volume response of the patient circuit is determined during the supply of air into the inspiratory line of the patient circuit 5. When, during the pre-use check of the ventilator 1, the determination of the volume of the patient circuit ($V_{pc}$) is made, the control unit 15 opens the expiratory valve 13 of the ventilator, still during occlusion of the proximal part of the patient circuit 5, and causes the ventilator 1 to switch from delivery of air to delivery of oxygen. A gas meter in form of an oxygen sensor (not shown), located downstream the part of the patient circuit 5 in which the humidifier 35 is located, measures the oxygen concentration of gas downstream said part of the patient circuit 5 and communicates the result of said measurements to the control unit 15 of the ventilator 1. The oxygen sensor may be located in the Y-piece 23 or the expiratory line of the patient circuit 5, or in an expiratory module of the ventilator 1. The control unit 15 is configured to determine the rate of change in oxygen concentration of the gas measured upon, based on the received measurement values. In one embodiment this is achieved by determining the time elapsed from the start of oxygen delivery by the ventilator 1 to the point in time at which the measured oxygen concentration reaches 90%, i.e. the time it takes to cause an increase in oxygen concentration from 21% (air) to 90%.

Figure 2A:
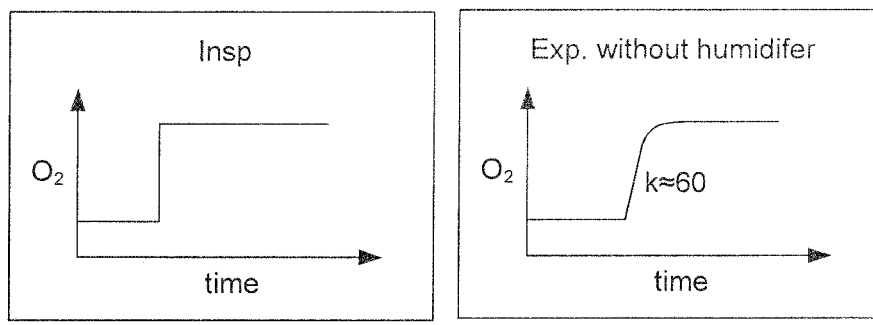
FIG. 2A illustrates a graph representing measured oxygen concentration over time upon delivery of oxygen into an inspiratory line of an air-containing patient circuit, measured downstream a part of the inspiratory line not comprising any humidifier.
Figure 2B:
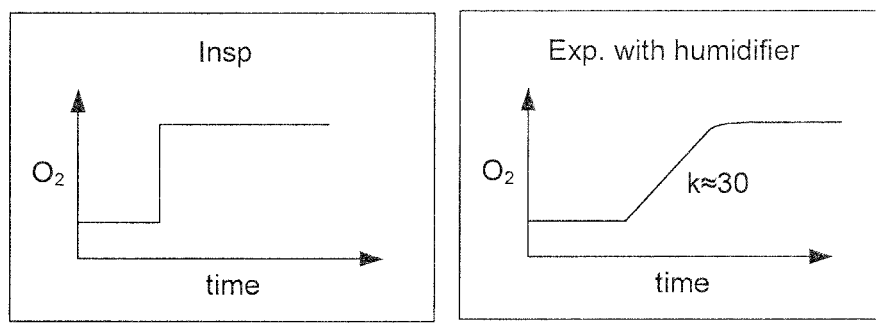
FIG. 2B illustrates a graph representing measured oxygen concentration over time upon delivery of oxygen into an inspiratory line of an air-containing patient circuit, measured downstream a part of the inspiratory line comprising a humidifier.

FIGS. 2A and 2B illustrate the difference in measured oxygen concentration over time between a situation in which measurements are obtained downstream a part of the inspiratory line not comprising any humidifier (FIG. 2A) and a situation in which measurements are obtained downstream a part of the inspiratory line comprising a humidifier (FIG. 2B).

FIG. 2A illustrates measured oxygen concentration in the absence of any humidifier. The left-hand graph shows the oxygen concentration ($O_2$) of gas delivered by the ventilator 1 into the inspiratory line of the patient circuit 5, prior to and after said change from delivery of air to delivery of oxygen. The delivered oxygen concentration is seen to increase almost momentarily from a first level of oxygen concentration in air (21%) to a second level of oxygen concentration (100%) in pure oxygen. The right-hand graph shows the oxygen concentration of gas downstream the part of the patient circuit 5 in which a humidifier might be present, e.g. as measured by an oxygen sensor in the expiratory module of the ventilator 1. The measured response to the change in oxygen concentration is seen to be fairly quick. Based on the time elapsed from the start of oxygen delivery by the ventilator 1 to the point in time at which the measured oxygen concentration reaches 90%, the control unit may calculate the slope of the graph (k≈60), representing the mean rate of change in oxygen concentration from 21% to 90% of the gas measured upon.

FIG. 2B illustrates measured oxygen concentration in the presence of a humidifier in the inspiratory line of the patient circuit 5. Here, the response to the change in oxygen concentration is seen to be considerably slower due to the increased degree of mixing of air and oxygen caused by the presence of the humidifier. Here, the mean rate of change in oxygen concentration from 21% to 90% yields a slope coefficient around 30.

The control unit 15 may for example be programmed to assume that a humidifier is present in the inspiratory line of the patient circuit 5 if said slope coefficient falls below a predetermined threshold value.

It should thus be appreciated that the control unit 15 may be configured to determine if a humidifier is present in a part of the inspiratory line of the patient circuit 5 by comparing the rate of change in gas composition (in this exemplary case oxygen concentration) downstream said part of the inspiratory line with a predetermined threshold value. The rate of change may, in this context, be represented by the above discussed slope coefficient, the time required to cause the increase in oxygen concentration from 21% to 90% or any other parameter indicative of said rate of change.

Preferably, the control unit 15 is configured to determine if a humidifier is present in the inspiratory line of the patient circuit 5 not only based on the rate of change in measured oxygen concentration but also based on the determined (total) volume of the patient circuit. If this volume is bigger than the volume of a normal patient circuit, this too is an indication that a humidifier is present in the inspiratory line thereof. Therefore, the control unit is advantageously configured to establish if the determined volume of the patient circuit is bigger than the volume of a "normal" patient circuit, as described in the following.

During supply of oxygen by the ventilator 1 (i.e. after having switched from delivery of air to delivery of oxygen during the pre-use check), the control unit 15 is configured to receive measurements on gas pressure and gas flow, and to determine the resistance and the type of the patient circuit 5 based on said pressure and flow measurements. Flow measurements may for example be provided to the control unit 15 by means of the above mentioned flow sensor in the inspiratory module of the ventilator 1, and pressure measurements may be provided by the above mentioned pressure sensor in the Y-piece 23 of the patient circuit 5 or the expiratory module of the ventilator 1.

The control unit 15 is preferably configured to first cause delivery of a flow of oxygen of 10 lpm, and to calculate the resistance of the patient circuit based on the thus obtained pressure and flow values. If the resistance is high, meaning that it exceeds a predetermined threshold value, the control unit 15 is programmed to conclude that the patient circuit 5 is a neonatal type of patient circuit 5, whereby no further resistance measurements are performed and the resistance value already derived is used to compensate for resistive losses of the patient circuit 5 during subsequent ventilation of the (neonatal) patient. If, on the other hand, the resistance is low or relatively low (below said threshold value), the control unit 15 is configured to conclude that the patient circuit 5 is an adult type of patient circuit, and to cause delivery of an increased flow of oxygen through the patient circuit 5, e.g. a flow of 60 lpm. Based on the pressure values obtained at the increased flow level, the control unit 5 calculates a new resistance value which is used by the control unit 15 during subsequent ventilation of the (adult) patient 3 to compensate for resistive losses of the patient circuit 5.

The measurement of the patient circuit resistance thus serves the double purposes of determining the type of the patient circuit and the resistive losses of the patient circuit.

Once the type of the patient circuit 5 has been determined, the control unit 15 can determine whether the determined volume of the patient circuit is bigger than "normal". To this end, the ventilator may store, e.g. in a digital memory thereof, a plurality of reference values indicative of typical volumes of patient circuits of different types, e.g. one reference value indicative of the volume of a typical neonatal patient circuit and one reference value indicative of the volume of a typical adult patient circuit. The control unit 15 may then compare the determined volume of the patient circuit 5 with the relevant reference value in dependence of the determined type of patient circuit, and determine whether or not the determined volume of the patient circuit is bigger than normal based on said comparison.

If the response to the change in oxygen concentration is quick and the determined volume of the patient circuit ($V_{pc}$) is not bigger than normal, then the control unit 15 is programmed to conclude that no humidifier is present in the inspiratory line of the patient circuit 5. If, however, the response to the change in oxygen concentration is slow and the determined volume of the patient circuit ($V_{pc}$) is bigger than normal, then the control unit 15 is programmed to conclude that a humidifier is present in the inspiratory line of the patient circuit 5.

Once the control unit 15 has determined whether the inspiratory line of the patient circuit 5 comprises a humidifier or not, the volume of the inspiratory line ($V_{insp}$) may be determined based on the total volume of the patient circuit ($V_{pc}$) and the presence of any humidifier. For example, as described above, the volume of the inspiratory line may be determined by the control unit as 50% of the total volume of the patient circuit in case of absence of any humidifier, and as 55%-65% of the total volume of the patient circuit in case of presence of a humidifier.

In one embodiment, the control unit 15 may be configured to, if a humidifier is deemed to be present, determine the volume of the inspiratory line more precisely from the total volume of the patient circuit and the type of the humidifier.

Typically, there is one type of humidifiers used for adult patient circuits (hereinafter referred to as adult humidifiers) and one type of humidifiers used for neonatal/pediatric patient circuits (hereinafter referred to as neonatal humidifiers). Before use, the humidifier is partly filled with water such that breathing gas passing through the humidifier is humidified before being delivered to the patient. The volume of the humidifier not filled by water adds volume to the inspiratory line of the patient circuit. This volume is typically 300 ml for an adult humidifier and 200 ml for a neonatal humidifier.

The control unit 15 may be configured to determine the type of the humidifier based on the type of the patient circuit currently connected to the ventilator 1, determined in accordance with the above described principles. If the patient circuit is determined to be an adult patient circuit, then the humidifier is assumed to be an adult humidifier. If, on the other hand, the patient circuit is determined to be a neonatal/pediatric patient circuit, then the humidifier is assumed to be a neonatal humidifier.

For example, the control unit 15 may be configured to determine the inspiratory line volume as 55%-60% of the total volume of the patient circuit if the humidifier is assumed to be a neonatal humidifier, and as 60%-65% of the total volume of the patient circuit if the humidifier is assumed to be an adult humidifier.

The control unit 15 may also be configured to determine the volume of the inspiratory line of the patient circuit based on the total volume of the patient circuit and the volume of the humidifier itself. To this end, the control unit 15 may for example be configured to store a look-up table of typical humidifier volumes associated with different types of humidifiers, e.g. 300 ml for adult humidifiers and 200 ml for neonatal humidifiers, and to use these humidifier volumes in the determination of the inspiratory line volume. The control unit 15 may select the humidifier volume associated with the determined type of humidifier, and calculate the volume of the inspiratory line based on the so selected humidifier volume and the total volume of the patient circuit. In one exemplary embodiment, the control unit 15 is configured to calculate the volume of the inspiratory line of the patient circuit using the following relationship:

$$V_{insp}=(V_{pc}-V_h)/2+V_h, \quad (eq.\ 7)$$

where $V_{insp}$ is the volume of the inspiratory line of the patient circuit, $V_{pc}$ is the total volume of the patient circuit, and $V_h$ is the active volume of the humidifier conveying breathing gas from the ventilator towards the patient, typically corresponding to the humidifier volume not filled by water. The determined volume of the inspiratory line may then be stored in a digital memory of the ventilator 1 for subsequent use during ventilation of the patient 3, and in particular upon activation of the oxygen boost function of the ventilator 1.

When, during ventilation of the patient 3, the operator activates the oxygen boost function, the control unit 15 retrieves the volume of the inspiratory line from memory and uses it together with current ventilation settings in order to determine the delay in delivery of the oxygen-enriched gas to the patient 3. Said current ventilation settings typically includes the current minute ventilation of the patient 3, which may be a set parameter or calculated by the control unit based on tidal volume and respiratory rate settings. Preferably, the control unit is configured to determine the net ventilation of the patient 3 from the current minute ventilation of the patient 3 and information related to leakage in the ventilation system, and to determine the delay in delivery of the oxygen-enriched gas to the patient 3 from the determined volume of the inspiratory line and said net ventilation of the patient 3.

Figure 3A:
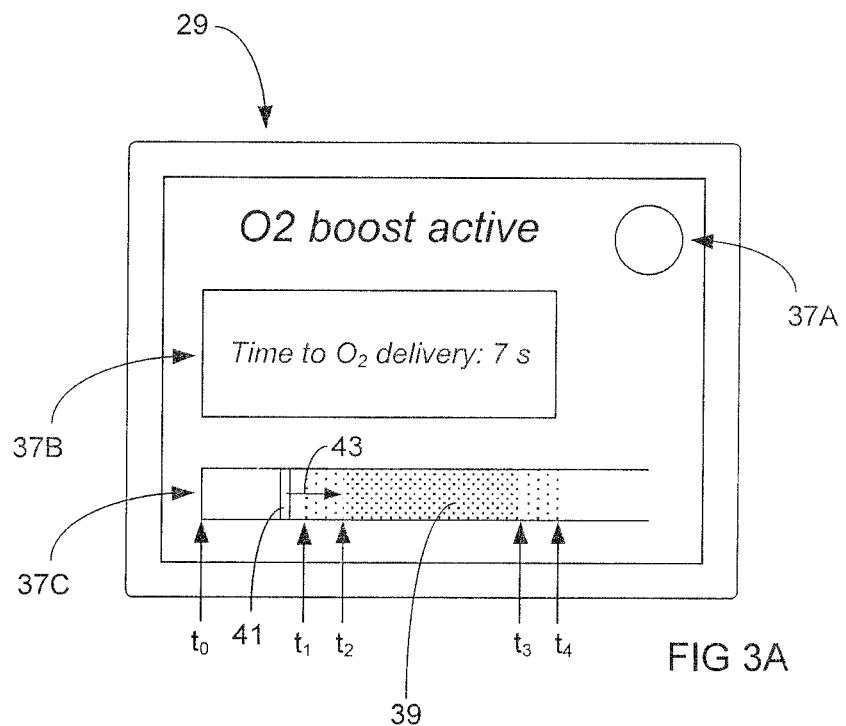
FIGS. 3A and 3B illustrate an exemplary GUI of a ventilator according to an exemplary embodiment of the present disclosure, which GUI is configured to indicate a delay in delivery of oxygen-enriched breathing gas from the ventilator to the patient upon activation of the oxygen boost function of the ventilator.
Figure 3B:
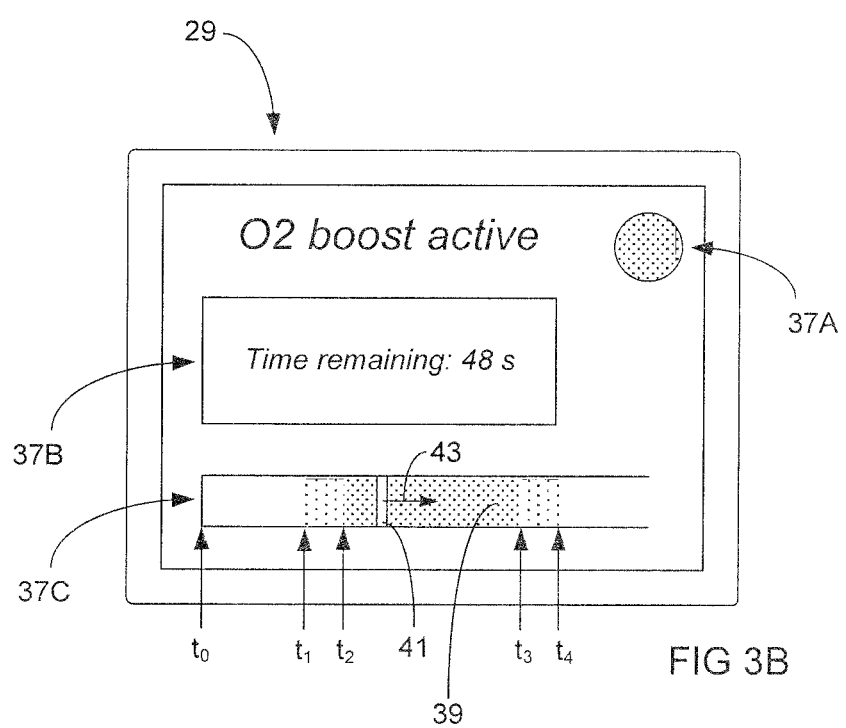

FIGS. 3A and 3B illustrate an exemplary embodiment of a GUI (graphical user interface) that may be caused by the control unit 15 to be displayed on the display unit 29 of the ventilator 1 upon activation of the oxygen boost function by the operator. The GUI comprises three examples of indicators 37A-C which may be displayed separately or in different combinations to indicate the delay in delivery of oxygen-enriched gas to the patient 3. FIG. 3A illustrates the appearance of said indicators 37A-C at a point in time after activation of the oxygen boost function but prior to delivery of the oxygen-enriched gas to the patient, whereas FIG. 3B illustrates the appearance of the indicators 37A-C at a later point in time, during delivery of the oxygen-enriched gas to the patient.

The first indicator 37A is a symbol, such as a circle, which is displayed in a colour selected in dependence of said delay. Upon activation of the oxygen boost function, the control unit 15 causes the indicator 37A to be displayed in a first colour (e.g. red) indicating that the oxygen-enriched breathing gas has not yet reached the patient. After a time period corresponding to said delay, the control unit 15 causes the indicator 37A to switch from the first colour to a second colour (e.g. green) indicating that oxygen-enriched breathing gas is now being delivered to the patient 3. After a yet another time period corresponding to the oxygen boost duration, the control unit causes the indicator 37A to switch back to the first colour to indicate that the patient has received oxygen-enriched breathing gas for the entire oxygen boost duration and that the oxygen concentration of the breathing gas currently being delivered to the patient is back at the baseline level.

The second indicator 37B is a text-based indicator indicating the time remaining to the next substantial change in oxygen concentration of the breathing gas reaching the patient, as determined from said delay. As indicated in FIG. 3A, the second indicator 37B may indicate, after activation of the oxygen boost function but prior to delivery of the oxygen-enriched breathing gas to the patient, the time remaining until a start point in time at which the patient starts to receive oxygen-enriched breathing gas. As indicated in FIG. 3B, the second indicator 37B may also indicate, once the oxygen-enriched breathing gas has started to reach the patient 3, the time remaining to a finish point in time at which the patient has received oxygen-enriched breathing gas during a time period corresponding to the set oxygen boost duration.

The third indicator 37C is an indicator indicating a wash-in-wash-out process of oxygen content in the breathing gas reaching the patient 3, caused by the activation of the oxygen boost function. To this end, the third indicator 37C comprises an elongated field 39 representing a time line, and an indicator 41 indicating the current point in time in relation to said time line. In this exemplary embodiment, the indicator 41 indicating the current point in time moves along the elongated field 39 as time goes by, as indicated by the arrow 43. The elongated field 39 comprises indications of at least a start point in time, $t_2$, at which breathing gas at said set oxygen boost level (typically 100% oxygen) reaches the patient 3, and a finish point in time, $t_3$, at which breathing gas at said set oxygen boost level has been delivered to the patient for a time period corresponding to the set oxygen boost duration. The elongated field 39 may further comprise any or any combination of an indication of the point in time, $t_0$, of activation of the oxygen boost function; an indication of a point in time, $t_1$, at which the oxygen content in the breathing gas reaching the patient 3 starts to increase from the baseline level towards the set oxygen boost level, and an indication of a point in time, $t_4$, at which the oxygen content in the breathing gas reaching the patient 3 starts to decrease from the set oxygen boost level towards the baseline level. Said indications may for example be provided by causing different areas of the elongated field 39 to be displayed in different colours. An area may in this context be an area of the elongated field 39 between any two of said points in time, $t_0$-$t_4$. For example, areas of the elongated field 39 representing delivery to the patient 3 of oxygen concentration at the baseline level (i.e. the area between to and $t_1$ and the area following $t_4$) may have one colour, areas of the elongated field 39 representing delivery to the patient 3 of increasing or decreasing oxygen concentration (i.e. the area between $t_1$ and $t_2$ and the area between $t_3$ and $t_4$) may have another colour, and the area of the elongated field 39 representing delivery to the patient 3 of oxygen concentration at the set oxygen boost level (i.e. the area between $t_2$ and $t_3$) may have yet another colour.

Figure 4:
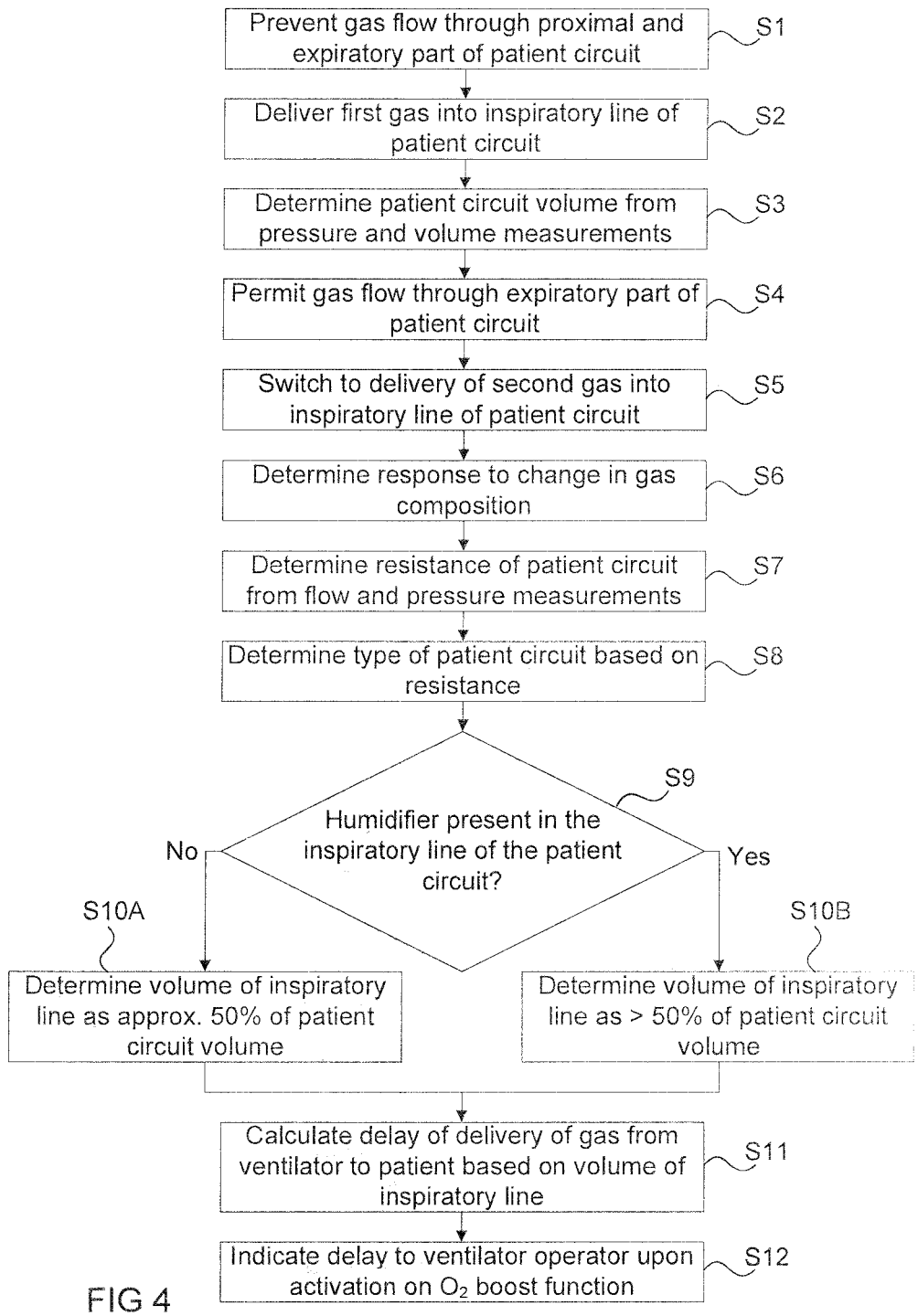
FIG. 4 illustrates an exemplary embodiment of a method for providing improved oxygen boost functionality of a ventilator according to the principles of the present disclosure.

FIG. 4 illustrates an exemplary embodiment of a method for providing improved oxygen boost functionality of a ventilator according to the principles of the present disclosure. The method will be described with simultaneous reference to previous drawings.

Steps S1 to S10 (A or B) are typically performed by the control unit 15 of the ventilator during the pre-use check of the ventilator 1, prior to connection of the patient 3 to the ventilator. Steps S11 and S12 are typically performed by the control unit 15 upon activation of the oxygen boost function by an operator of the ventilator.

In the first step S1, gas flow through the proximal and expiratory parts of the patient circuit 5 is prevented. As described above, this may be achieved by the control unit 15 through the display of an instruction to manually occlude the proximal part of the patient circuit on the display unit 29 of the ventilator 1, and closure of the expiratory valve 13 of the ventilator.

In a next step S2, a first gas, typically air, is delivered into the inspiratory line of the patient circuit 15.

In a next step S3, the patient circuit volume, $V_{pc}$, i.e. the total volume of the inspiratory line and the expiratory line of the patient circuit, is determined from pressure and volume measurements. As described above, this is typically achieved by determining a pressure-to-volume response of the patient circuit, assuming the compliance, $C_{pc}$, of the tubing of the patient circuit to be negligible and taking surrounding pressure, $P_{amb}$, into account.

In a next step S4, action is taken to now permit gas flow through the expiratory part of the patient circuit 5, typically by opening said expiratory valve 13 of the ventilator 1.

In a next step S5, a second gas, typically oxygen, is delivered into the inspiratory line of the patient circuit 5.

In a next step S6, a response to the change in gas composition in the patient circuit 5, caused by the introduction of the second gas into the inspiratory line, is determined. As described above, this involves determination of a parameter indicative of the rate of change in gas composition downstream a part of the inspiratory line in which a humidifier may or may not be present.

In a next step S7, typically carried out in parallel with step S6, the resistance of the patient circuit is determined from flow and pressure measurements.

In a next step S8, the type of the patient circuit 5 currently connected to the ventilator 1 is determined from the resistance of the patient circuit 5, determined in step S7.

In a next step S9, it is determined whether the inspiratory line of the patient circuit comprises any humidifier. This determination is made based on the response to the change in gas composition in the patient circuit, determined in step S6. Preferably, it is also made based on the volume of the patient circuit, determined in step S3, taking the type of the patient circuit determined in step S8 into account.

In the next steps S10A and S10B, the volume of the inspiratory line of the patient circuit 5 is determined in dependence of the total volume of the patient circuit 5, determined in step S3, and the presence of any humidifier in the inspiratory line, as determined in step S9.

If no humidifier is determined to be present in step S9, the method continues to step S10A. If, on the other hand, a humidifier is determined to be present, the method continues to step S10B.

In step S10A, the volume of the inspiratory line of the patient circuit is determined to constitute approximately 50% of the total volume of the patient circuit since the inspiratory line volume substantially equals the expiratory line volume in the absence of any humidifier in the inspiratory line.

In step S10B, the volume of the inspiratory line of the patient circuit is determined to constitute the majority part of the total volume of the patient circuit since the presence of a humidifier adds considerable volume to the inspiratory line. As described above, in this scenario, the volume of the inspiratory line may be assumed to constitute e.g. 55%-65% of the total volume of the patient circuit, or be calculated more precisely using e.g. equation 7.

In a next step S11, typically taking place after connection of a patient 3 to the ventilator 1 and upon activation of the oxygen boost function of the ventilator, a delay in delivery of gas from the ventilator to the patient is calculated based on the volume of the inspiratory line, determined in step S10A or S10B. As described above, said delay is typically determined based on the volume of the inspiratory line together with the current minute ventilation (preferably net ventilation) of the patient 3.

In a next step S12, an indication of said delay is communicated to the operator of the ventilator 1, typically through the display of an indicator indicating said delay on a display unit 29 of the ventilator.

The invention claimed is:

1. A ventilator for delivering a breathing gas to a patient, comprising:
   a control unit,
   wherein the breathing gas is delivered via a patient circuit, the patient circuit connecting the ventilator and the patient, the ventilator being configured to, upon activation of an oxygen boost function of the ventilator, increase an oxygen concentration of the breathing gas so as to deliver the oxygen-enriched breathing gas to the patient, and
   wherein the control unit is configured to (a) determine a volume of a part of the patient circuit conveying the breathing gas from the ventilator to the patient, (b) determine a delay in delivery of the oxygen-enriched breathing gas to the patient based on the volume, and (c) cause an indication of the delay to an operator of the ventilator, and (d) calculate, based on the delay, a start point in time at which the oxygen-enriched breathing gas reaches the patient and (e) cause an indication of the start point in time to the operator of the ventilator.

2. The ventilator according to claim 1, wherein the ventilator, upon activation of the oxygen boost function, is configured to deliver the oxygen-enriched breathing gas during a set period of time, the control unit being configured to (a) calculate, based on the delay and the set period of time, a finish point in time at which the oxygen-enriched breathing gas has been delivered to the patient for the set period of time and (b) cause an indication of the finish point in time to the operator of the ventilator.

3. The ventilator according to claim 2, wherein the control unit is configured to cause an indication of the time remaining until the finish point in time.

4. The ventilator according to claim 1, wherein the control unit is configured to cause an indication of a wash-in-wash-out process of oxygen content in the breathing gas reaching the patient, caused by the activation of the oxygen boost function.

5. The ventilator according to claim 1, further comprising:
a display unit connected to the control unit,
wherein the control unit is configured to cause the indication by causing display of an indicator on of the display unit.

6. The ventilator according to claim 1, wherein the control unit is configured to cause the indication by causing display of an indicator on a display unit of a monitoring system to which the ventilator is connected.

7. The ventilator according to claim 1, wherein the indicator is a dynamic indicator indicating whether the breathing gas currently reaching the patient is the oxygen-enriched breathing gas or not.

8. The ventilator according to claim 7, wherein the indicator indicates one of at least two colours, a first colour of the at last two colours representing a first state in which the oxygen-enriched breathing gas is delivered to the patient, a second colour of the at least two colours representing a second state in which the non-oxygen-enriched breathing gas is delivered to the patient, the indicator indicating one of the at least two colours in dependence of whether the breathing gas currently reaching the patient is the oxygen-enriched breathing gas or the non-oxygen-enriched breathing.

9. The ventilator according to claim 1, wherein the ventilator, upon the activation of the oxygen boost function, is configured to increase the oxygen concentration of the breathing gas to a set level of the oxygen concentration, the oxygen-enriched breathing gas being the breathing gas having the set level of oxygen concentration.

10. The ventilator according to claim 1, wherein the control unit is configured to automatically determine the volume of the part of the patient circuit based on information related to pressure changes in response to changes in a gas volume in the patient circuit.

11. The ventilator according to claim 1, wherein the control unit is configured to determine the volume of the part of the patient circuit during a pre-use check of the ventilator, prior to connection of the patient to the ventilator, during prevention of a gas flow through a proximal and expiratory part of the patient circuit.

12. The ventilator according to claim 1, wherein the control unit is configured to (a) automatically determine if a humidifier is present in a part of the patient circuit conveying the breathing gas from the ventilator to the patient and (b) determine a volume of the part of the patient circuit based on the presence of the humidifier.

13. A method for providing an improved oxygen boost functionality of a ventilator delivering breathing gas to a patient via a patient circuit, the patient circuit connecting the ventilator and the patient, the ventilator being configured to, upon an activation of an oxygen boost function of the ventilator, increase an oxygen concentration of the breathing gas so as to generate oxygen-enriched breathing gas to be delivered to the patient, the method comprising the steps of:
determining a volume of a part of the patient circuit conveying the breathing gas from the ventilator to the patient;
determining a delay in delivery of the oxygen-enriched breathing gas to the patient based on the volume, and causing an indication of the delay to an operator of the ventilator, and—calculating, based on the delay, a start point in time at which the oxygen-enriched breathing gas reaches the patient, and—causing an indication of the start point in time to the operator of the ventilator.

14. A computer program for providing an improved oxygen boost functionality of a ventilator delivering breathing gas to a patient via a patient circuit, the patient circuit connecting the ventilator and the patient, the ventilator being configured to, upon an activation of an oxygen boost function of the ventilator, increase an oxygen concentration of the breathing gas so as to generate the oxygen-enriched breathing gas to be delivered to the patient, the computer program comprising computer-readable program code which, when executed, causes a control unit of the ventilator to perform steps of claim 13.

15. A ventilator for an automatic determination of a presence of a humidifier in an inspiratory line of a patient circuit, the ventilator being connected the patient circuit, the ventilator comprising:
a control unit configured to:
cause a change in a gas composition in the patient circuit through a supply into the inspiratory line of a gas having a different composition than another gas previously occupying the patient circuit;
determine a rate of change in the gas composition downstream a part of the inspiratory line, and
determine if the humidifier is present in the part of the inspiratory line based on the rate of change in the gas composition.

* * * * *

UNITED STATES PATENT AND TRADEMARK OFFICE
CERTIFICATE OF CORRECTION

PATENT NO. : 10,737,050 B2
APPLICATION NO. : 15/736256
DATED : August 11, 2020
INVENTOR(S) : Selander Page 1 of 1

It is certified that error appears in the above-identified patent and that said Letters Patent is hereby corrected as shown below:

In the Claims

Claim 7, Column 21, Line 33:
"The ventilator according to claim 1, wherein the" should read "The ventilator according to claim 5, wherein the"

Claim 8, Column 21, Line 39:
"of the at last two colours respresenting a first state in which" should read "of the at least two colours representing a first state in which"

Claim 8, Column 21, Line 47:
"riched breathing." should read "riched breathing gas."

Claim 13, Column 22, Line 26:
"breathing gas to the patient based on the volume, and" should read "breathing gas to the patient based on the volume;"

Claim 13, Column 22, Lines 28 and 29:
"ventilator, and - calculating, based on the delay, a start point in time at which the oxygen-enriched breathing" should read
"ventilator; and
    calculating, based on the delay, a start in time at which the oxygen-enriched breathing"

Claim 15, Column 22, Line 45:
"circuit, the ventilator being connected the patient circuit, the" should read "circuit, the ventilator being connected to the patient circuit, the"

Signed and Sealed this
Twelfth Day of January, 2021

Andrei Iancu
*Director of the United States Patent and Trademark Office*